United States Patent
Lafitte et al.

(10) Patent No.: US 7,092,849 B2
(45) Date of Patent: Aug. 15, 2006

(54) EXTRACTING CAUSAL INFORMATION FROM A CHAOTIC TIME SERIES

(75) Inventors: Melvyn Jérémie Lafitte, Prevessin-Moens (FR); Orin Sauvageot, Geneva (CH); Marion Fèvre-Genoulaz, Cernex (FR); Srini Nageshwar, Los Gatos, CA (US)

(73) Assignee: Dyansys, Inc., Burlingame, CA (US)

( * ) Notice: Subject to any disclaimer, the term of this patent is extended or adjusted under 35 U.S.C. 154(b) by 0 days.

(21) Appl. No.: 10/961,710

(22) Filed: Oct. 7, 2004

(65) Prior Publication Data

US 2005/0075811 A1    Apr. 7, 2005

Related U.S. Application Data

(63) Continuation-in-part of application No. PCT/IB03/02522, filed on Jun. 27, 2003.

(51) Int. Cl.
G06F 11/30 (2006.01)
G06F 19/00 (2006.01)
G21C 17/00 (2006.01)
H04B 15/00 (2006.01)

(52) U.S. Cl. ......................... 702/183; 702/190; 702/70
(58) Field of Classification Search .................. 702/66, 702/69, 70, 79, 183, 189–191, 195
See application file for complete search history.

(56) References Cited

U.S. PATENT DOCUMENTS

| | | | |
|---|---|---|---|
| 5,285,793 A | 2/1994 | Slovut et al. | |
| 5,349,962 A | 9/1994 | Lockard et al. | |
| 5,645,070 A | 7/1997 | Turcott | |
| 5,971,922 A | 10/1999 | Arita et al. | |
| 6,999,445 B1 * | 2/2006 | Dmitriev et al. | 370/342 |

FOREIGN PATENT DOCUMENTS

| | | | |
|---|---|---|---|
| WO | 00/74331 | * | 12/2000 |
| WO | 2005/001706 | * | 1/2005 |

OTHER PUBLICATIONS

Abarbanel, H. D. I., "The analysis of observed chaotic data in physical systems," *Reviews of Modern Physics, American Physical Society*, 65(4):1331-1392 (1993).

* cited by examiner

*Primary Examiner*—Michael Nghiem
(74) *Attorney, Agent, or Firm*—Townsend and Townsend and Crew LLP

(57) ABSTRACT

Embodiments of the present invention provide a method, a system, and a computer code for analyzing the state of a first system (e.g., the autonomic system) from a time-varying signal representing a chaotic series of time intervals between quasi-periodical events produced by a second system (e.g., the cardiac system) governed by the first system. In one embodiment, the method includes extracting envelope information from the time-varying signal, constructing a phase space for the time-varying signal, extracting information on the relative positions of points corresponding to the time-varying signal in the phase space, combining the envelope and the position information and, based on this combination, providing information on the state of the first system.

65 Claims, 12 Drawing Sheets

EXTRACTING CAUSAL INFORMATION FROM A CHAOTIC TIME SERIES

CROSS-REFERENCES TO RELATED APPLICATIONS

This application is a continuation-in-part of, and claims priority under 35 U.S.C. § 120 from, International Patent Application No. PCT/IB 03/02522, filed Jun. 27, 2003, the entire disclosure of which is incorporated herein by reference.

BACKGROUND OF THE INVENTION

The present invention relates generally to a method and apparatus for extracting causal information from a chaotic time series. More particularly, the present invention pertains to a method and apparatus for analyzing the state of a first system from a time-varying signal representing a chaotic series of time intervals between quasi-periodical events produced by a second system governed by the first system. In a typical, but non-exclusive, application of the invention, the first system is the autonomic nervous system (ANS) and the second system is the cardiac system.

Measures of heart rate variability (HRV) have been shown to be a powerful means of assessing the influence of the ANS on the cardiac system. Indeed, the ANS, with its sympathetic and parasympathetic subsystems, governs involuntary actions of the cardiac muscle and every visceral organs in the body.

The ANS is not directly accessible to voluntary control. Instead, it operates in an autonomic fashion on the basis of autonomic reflexes and central control. One of its major functions is the maintenance of homeostasis within the body. The ANS further plays an adaptive role in the interaction of the organism with its surroundings.

In many diseases, the sympathetic and/or parasympathetic parts of the ANS are affected leading to autonomic dysfunction. It is then important to have reliable and representative measures of the activity and the state of the ANS.

Three main classes of methods are used to recover information about the ANS from the heart rate variability: spectral analysis (also called time domain analysis), statistics and calculation of a correlation dimension (or any related dimension). These methods do not give easy interpretable outcomes. Moreover, they lack reliability and are not mathematically appropriate in their considered application.

BRIEF SUMMARY OF THE INVENTION

Embodiments of the present invention provide a method, a system, and a computer code for analyzing the state of a first system (e.g., the autonomic system) from a time-varying signal representing a chaotic series of time intervals between quasi-periodical events produced by a second system (e.g., the cardiac system) governed by the first system.

An aspect of the present invention is directed to a method for analyzing the state of a first system from a time-varying signal representing a chaotic series of time intervals between quasi-periodical events produced by a second system governed by the first system. The method comprises extracting envelope information from the time-varying signal, constructing a phase space for the time-varying signal, extracting information on the relative positions of points corresponding to the time-varying signal in the phase space, combining the envelope and the position information and, based on this combination, providing information on the state of the first system.

Thus, the present invention exploits the fractal geometry of the time-varying signal and combines an envelope calculation scheme with an evaluation of the dispersion of points in a reconstructed phase space. The present inventors have found that such a combination enables emphasizing the variations of significance in the chaotic series of time intervals while dismissing the variations of no significance, thus providing precise information on the state of the first, underlying system.

A more dynamic and reactive response to a change in the state of the first system may be obtained in the invention by calculating two envelopes for the series of time intervals, namely a first upper envelope calculated in the direction of the chronological order and a second upper envelope calculated in the direction opposite to the chronological order.

The present invention makes also possible to discriminate the sympathetic and parasympathetic components of the ANS and, by means of the different calculations presented herein below, to describe the instantaneous state of each of these components.

DETAILED DESCRIPTION OF THE INVENTION

Figure 1:
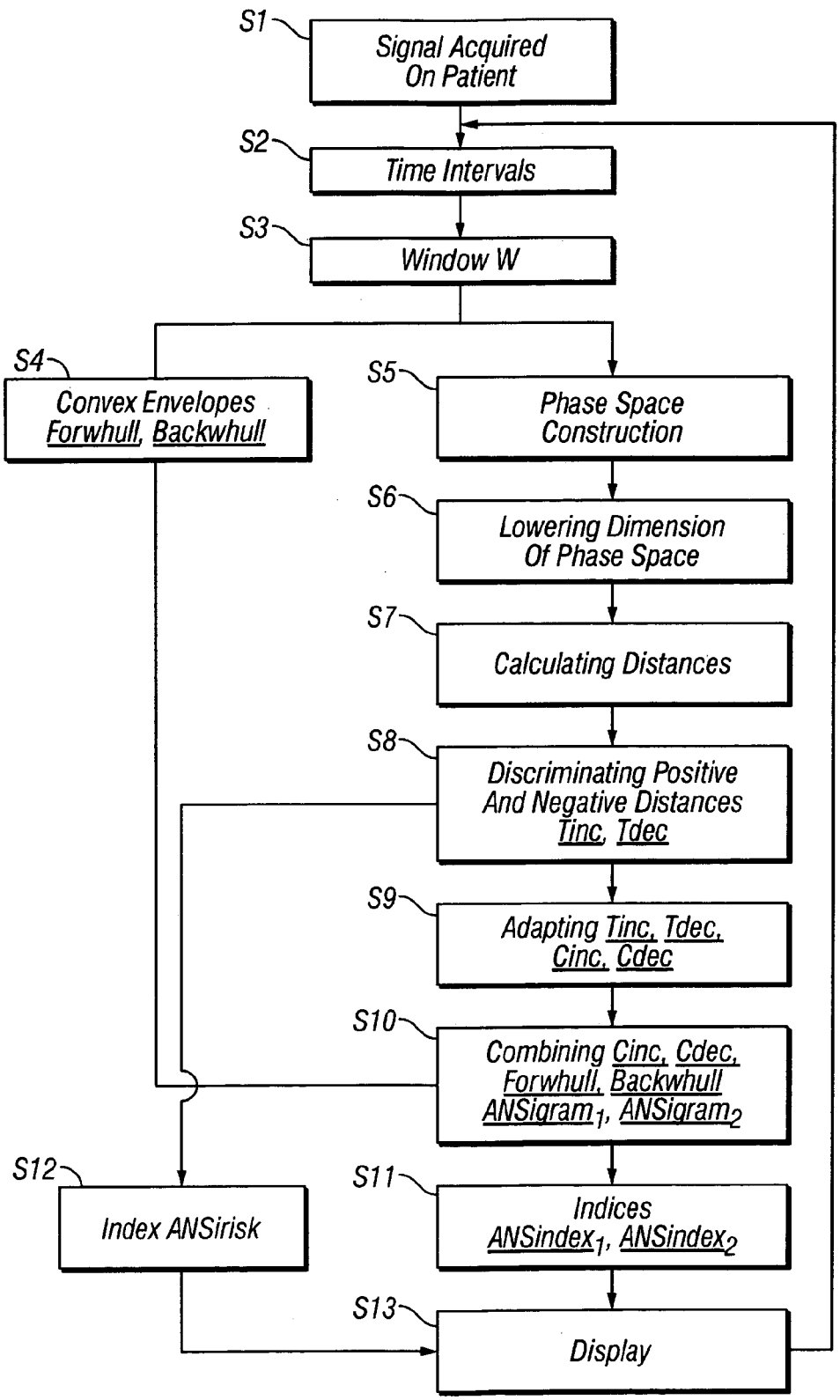
FIG. 1 is a flow chart of the method according to one embodiment of the invention.

With reference to FIG. 1, a method for analyzing the state of the ANS comprises steps S1 to S13.

In step S1, a first time-varying signal or data representing quasi-periodical events produced by a biological system governed by the ANS of a patient is acquired. The said biological system is, for example, the cardiac, respiratory or brain system of the patient. The first time-varying signal is a raw signal, i.e., a non-smoothed and non-filtered signal. Thus, all variations of this signal are kept, including microvariations.

Figure 5:
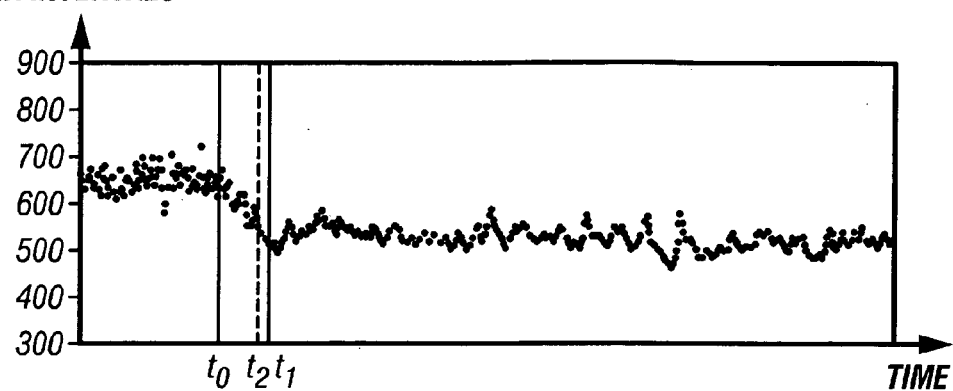
FIG. 5 shows a time-varying signal representing RR intervals derived from an electrocardiogram.

In step S2, the quasi-periodical events in the first time-varying signal are detected and the time intervals between these quasi-periodical events are calculated so as to form a second time-varying signal or data, called "time-interval signal", taking discrete values consisting of the series of calculated time intervals. Such a series of time intervals is known to be chaotic. In a preferred embodiment of the invention, the time-varying signal acquired in step S1 is the electrocardiogram (ECG) of the patient and the time intervals calculated in step S2 are the RR intervals, i.e., the intervals between the R waves of the ECG. FIG. 5 shows, by way of illustration, an example of a time-interval signal obtained in step S2 in the case of such RR intervals. Each point in the signal of FIG. 5 corresponds to a calculated time interval. Such a signal is known in the art as being fractal.

In practice, step S2 is performed in real time, i.e., each time an event occurs in the first time-varying signal, this event is detected and the time interval between this event and the preceding one is calculated. In the same manner, the algorithm formed by the following steps S3 to S13 is performed each time a time interval is calculated by step S2.

In step S3 a time window W is defined. The upper limit $L_1$ of time window W is the instant corresponding to the last time interval calculated in step S2. The lower limit $L_0$ is set such that the width $L_1-L_0$ of time window W corresponds to a predetermined number N of calculated time intervals. In other words, the window W encompasses the last (current) calculated time interval and the N-1 preceding calculated time intervals. The predetermined number N corresponds to the time scale in which the state of the ANS is to be determined and visualized. This number may be selected by the user. Its default value is, for example, 40.

Figure 2:
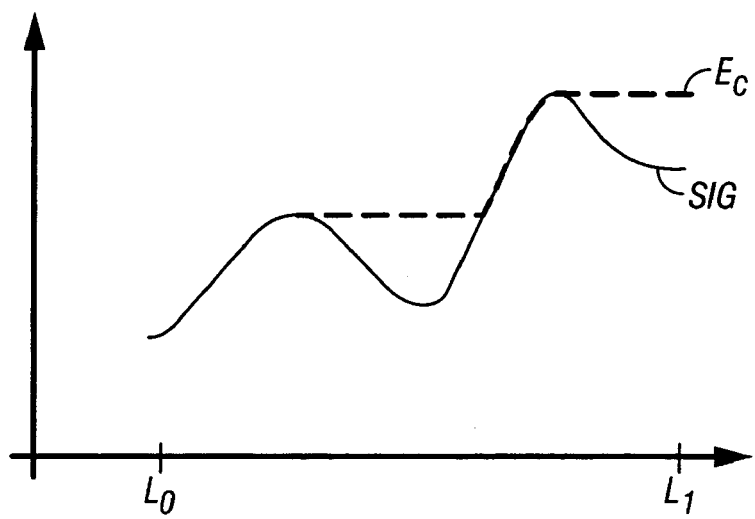
FIGS. 2 and 3 respectively show, as a general illustration, how two different envelopes, one determined in the direction of the chronological order and the other determined in the direction opposite to the chronological order, may be obtained from a given time-varying signal.
Figure 3:
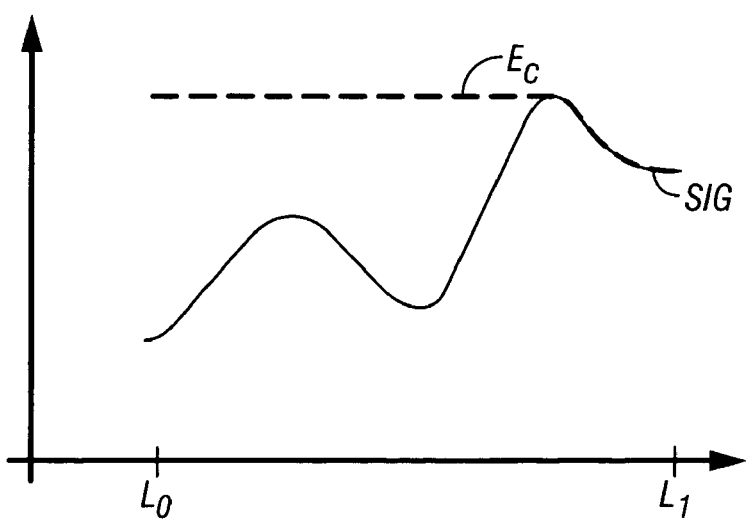

In step S4, two convex or upper envelopes of the time-interval signal obtained in step S2 are calculated in window W. One of these envelopes is calculated in the direction of the chronological (temporal) order, from the lower limit $L_0$ of time window W up to the upper limit $L_1$. The other one is calculated in the direction opposite to the chronological order, from the upper limit $L_1$ down to the lower limit $L_0$, and then reset in the chronological order. By way of general illustration, FIGS. 2 and 3 respectively show for a given arbitrary signal SIG in window W the corresponding upper envelope $E_c$ as calculated in the direction of the chronological order and the corresponding upper envelope $E_{nc}$ as calculated in the direction opposite to the chronological order. As is apparent from these figures, the two envelopes are different and thus contain different, complementary information on the variations of the signal SIG. It is recalled that the upper envelope of a given signal f(t) is given by the following formula:

$$f(s) = \max_{1 \leq t \leq s} f(t).$$

The upper envelopes as obtained in step S4 of the present embodiment are each in the form of a table or vector having N values, each of which corresponds to one of the discrete values taken by the time-interval signal. The table corresponding to the upper envelope calculated in the direction of the chronological order will be referred to in the following as ForwHull and the table corresponding to the upper envelope calculated in the direction opposite to the chronological order as BackwHull.

The sequence of step S5 to S10 is performed in parallel with step S4. Step S5 consists in constructing a several-dimensional phase space for the portion of the time-interval signal in window W. The notion of phase space is known per se in the field of mathematical physics. A scheme for construction of the phase space and reasons for this construction are described, for example, in the paper entitled "Geometry from a Time Series" by Packard et al., Physical Review Letters, Volume 45, Number 9, 1 Sep. 1980 and in the paper entitled "Predicting Chaotic Time Series" by Farmer et al., Physical Review Letters, Volume 59, Number 8, 24 Aug. 1987. The present embodiment follows this scheme and, as such, the phase space is constructed in the following manner: from the series of values taken by the time-interval signal in window W, designated by $X_1, X_2, X_3, \ldots, X_N$ from the lower limit $L_0$ to the upper limit $L_1$, vectors, e.g. three-dimensional, are constructed using a time lag or shift, e.g. of four. Thus, typically, the first vector will have as its first component the first value $X_1$ of the time-interval signal in window W, as its second component the fifth value $X_5$ of the time-interval signal in window W, and as its third component the ninth value $X_9$ of the time-interval signal in window W. The second vector will have as its first component the second value $X_2$ of the time-interval signal in window W and as its second and third components the sixth and tenth values $X_6$, $X_{10}$ of the time-interval signal in window W, and so on. Preferably, in order to obtain a number N of such vectors, the series of vectors is completed by repeating the last complete vector as many times as necessary at the end of the series. The vectors obtained are listed below:

$$\begin{pmatrix} X_1 \\ X_5 \\ X_9 \end{pmatrix}, \begin{pmatrix} X_2 \\ X_6 \\ X_{10} \end{pmatrix}, \begin{pmatrix} X_3 \\ X_7 \\ X_{11} \end{pmatrix}, \ldots, \begin{pmatrix} X_{N-8} \\ X_{N-4} \\ X_N \end{pmatrix}, \begin{pmatrix} X_{N-8} \\ X_{N-4} \\ X_N \end{pmatrix}, \ldots, \begin{pmatrix} X_{N-8} \\ X_{N-4} \\ X_N \end{pmatrix}.$$

Although in the preferred embodiment of the invention the dimension of the vectors, i.e., the dimension of the phase space, and the time lag are respectively equal to three and four, these dimension and time lag may be different. When such dimension and time lag are different, it is however preferable to keep their product equal to 12.

Figure 4:
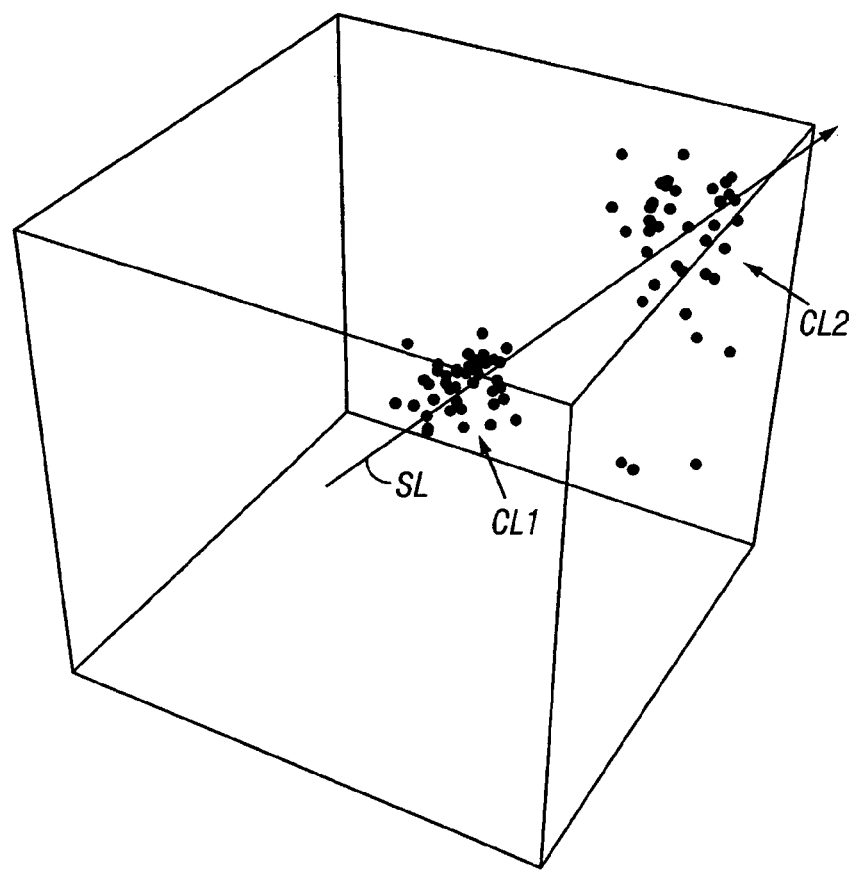
FIG. 4 diagrammatically shows an example of a phase space obtained in the method according to an embodiment of the invention.

The vectors obtained as described above each represent a point in the phase space. The present inventors have observed that, rather than being distributed randomly, the points of the phase space form clusters of points, each of which represents a common equilibrium state of the ANS. As an illustration, FIG. 4 shows the phase space obtained during a tilt test applied to a patient, i.e., a test in which the patient is levered from a horizontal position to a quasi-vertical one (angle of 80°). As can be seen, this phase space includes two separate clusters of points CL1, CL2. Each of these clusters of points CL1, CL2 corresponds to one of the above-mentioned horizontal and quasi-vertical positions.

Step S6 consists in lowering the dimension of the phase space in order to get information on the positions of the points relative to one another. Step S6 more specifically consists in orthogonally projecting the points of the phase space, i.e., the points corresponding to the above-mentioned vectors, onto a space of lower dimension on which an order relation can be established. Typically, step S6 projects the points of the phase space onto a straight line that minimizes the average distance between these points and the straight line. Such a straight line passes through the clusters of points, as shown in FIG. 4 at reference sign SL. It may be obtained through a conventional linear fit method. The straight line is given an orientation, which may be selected arbitrarily but preferably according to the axis of the phase space the straight line is most parallel to.

Once all the points of the phase space have been projected onto the above-mentioned straight line, step S7 calculates the relative distances between the projected points while respecting the chronological order of these points. Precisely, step S7 first calculates the distance between the first point in the chronological order, i.e., the projected point corresponding to the first vector or point $(X_1, X_5, X_9)$, and the second point in the chronological order, i.e., the projected point corresponding to the second vector or point $(X_2, X_6, X_{10})$, then between the first point and the third point in the chronological order, then between the first point and the fourth point in the chronological order, and so on. Then step S7 calculates the distance between the second point in the chronological order and the third point in the chronological order, then between the second point and the fourth point in the chronological order, then between the second point and the fifth point in the chronological order, and so on. Then step S7 calculates the distance between the third point and the fourth point in the chronological order, then between the third point and the fifth point in the chronological order, and so on. Step S7 thus calculates N(N+1)/2 distances. Due to the orientation given to the projection straight line on which the points are located, these distances are either positive or negative (the value zero being considered, for example, as a positive value). All these distances are set in a table and arranged therein in the order in which they have been calculated. Such a table is representative of an average distance between the clusters of points in the several-dimension phase space.

In step S8, the positive and negative distances calculated in step S7 are discriminated. More specifically, first and second tables Tinc, Tdec are created including respectively the positive distances and the absolute value of the negative distances, the values in each of these tables Tinc, Tdec keeping the same order as in their original table, that is the temporal order.

The tables Tinc, Tdec created in step S8 may have different lengths. In step S9, starting from the latest (most recent) temporal position in each of the tables Tinc, Tdec, the first encountered group of N successive values with highest mean average is chosen and kept in the table, the other values being dismissed, thus reducing the dimension of each of these tables to N. Furthermore, if one of these kept N values in the table Tinc or Tdec is lower than a predetermined value R, it is replaced in the corresponding table Tinc or Tdec by the preceding value in the group of N values. The predetermined value R may be selected by the user. This value R represents the minimum variation of time interval between events in the first time-varying signal considered as being of significance for the user. The two tables obtained at the end of step S9 will be referred to in the following as Cinc (table including the positive distances) and Cdec (table including the absolute value of the negative distances).

In step S10, the tables Cinc and Cdec are combined with the upper envelopes ForwHull and BackwHull to provide information on the instantaneous state of the ANS. To this effect, step 10 carries out two different calculations, called CT1 and CT2, which are exposed below:

CT1:
$$Coeffinc_1 = B + (4 - 4A - 5B + 4AB) \cdot Cinc - B \cdot Cdec$$
$$Coeffdec_1 = B - B \cdot Cinc + (4A - 4AB - B) \cdot Cdec$$
$$ANSigram_1 = 1 - \frac{2 \cdot normcoeff}{3} \cdot (Coeffinc_1 \cdot ForwHull + Coeffdec_1 \cdot BackwHull)$$

where A and B are predetermined constants which, in the preferred embodiment of the invention, are each equal to 0.5, normcoeff is a normalization coefficient, $Coeffinc_1 \cdot ForwHull$ is the term-by-term product of the tables $Coeffinc_1$ and ForwHull and $Coeffdec_1 \cdot BackwHull$ is the term-by-term product of the tables $Coeffdec_1$ and BackwHull;

CT2:
$$Coeffinc_2 = \frac{B}{3} + 4(1 - B) \cdot (1 - A) \cdot Cinc$$
$$Coeffdec_2 = \frac{B}{3} + 4(1 - B) \cdot A \cdot Cdec$$
$$ANSigram_2 = 1 - \frac{2 \cdot normcoeff}{3} \cdot (Coeffinc_2 \cdot ForwHull + Coeffdec_2 \cdot BackwHull)$$

where A and B are the same predetermined constants as in CT1, normcoeff is the same normalization coefficient as in CT1, $Coeffinc_2 \cdot ForwHull$ is the term-by-term product of the tables $Coeffinc_2$ and ForwHull and $Coeffdec_2 \cdot BackwHull$ is the term-by-term product of the tables $Coeffdec_2$ and BackwHull.

According to the present inventors, the table $ANSigram_1$ as obtained above by the calculation CT1 is representative of the state of the parasympathetic component of the ANS and the table $ANSigram_2$ as obtained above by the calculation CT2 is representative of the state of the sympathetic component of the ANS. Thus, the present embodiment not only provides information on the state of the ANS but can also discriminate the sympathetic and parasympathetic components of the ANS. In practice, as will be apparent in the following, each of the tables $ANSigram_1$ and $ANSigram_2$ will be presented to the user in the form of a curve linking the points of the table. The shape of this curve will be directly interpretable by the user. For example, flat $ANSigram_1$ and $ANSigram_2$ curves will indicate a low reactivity of the ANS whereas observing e.g. a persistent increasing slope in these curves will indicate a change of pace in the time intervals, i.e., in the case of the first time-varying signal being an ECG, a change of the cardiac activity. The user will also have the possibility to compare the morphology of these curves with previously seen curve morphologies to precisely identify a trouble affecting the patient. Furthermore, the point-by-point subtraction of one of the curves $ANSigram_1$ and $ANSigram_2$ from the other will give the user a view of the balance between the sympathetic and the parasympathetic subsystems, balance which was discovered by the present inventors to be non-linear.

In step S11, a first index $ANSindex_1$ is calculated for representing a complexity exponent of the table or curve $ANSigram_1$ and a second index $ANSindex_2$ is calculated for representing a complexity exponent of the table or curve $ANSigram_2$. The index $ANSindex_1$, respectively $ANSindex_2$, is a number which is high when the corresponding curve $ANSigram_1$, respectively $ANSigram_2$, exhibits large fluctuations and which is low when the curve $ANSigram_1$, respectively $ANSigram_2$, exhibits small fluctuations, i.e., is almost rectilinear. These indices are typically calculated as a Bouligand dimension normalized as exterior, for example in the following manner:

$$ANSindex_1 = \text{Floor}\left[\left(6 + \frac{9375}{12} \cdot \left(\frac{\log(ANSlength_1)}{\log\sqrt{range_1^2 + N^2}} - 1\right)\right) \cdot (\sqrt{5} + 1)\right]$$

$$ANSindex_2 = \text{Floor}\left[\left(6 + \frac{1875}{12} \cdot \left(\frac{\log(ANSlength_2)}{\log\sqrt{range_2^2 + N^2}} - 1.045\right)\right) \cdot (\sqrt{5} + 1)\right]$$

where Floor designates the integer part, which returns zero if the argument is negative, $ANSlength_1$ and $ANSlength_2$ respectively designate the length of the curve $ANSigram_1$ and the length of the curve $ANSigram_2$, range$_1$ designates the difference between the last value and the first value of the curve $ANSigram_1$ and range$_2$ designates the difference between the last value and the first value of the curve $ANSigram_2$.

In step S12 an index ANSirisk is calculated which represents a risk or probability that the shape of the curves $ANSigram_1$ and $ANSigram_2$ will change at the next event in the first time-varying signal (i.e., in the case of an ECG, at the next R wave detected), which would mean a probability of change of the state of the ANS. This index ANSirisk represents, in other words, the degree of activity of the ANS. The calculation of index ANSirisk is based on one of tables Tinc and Tdec obtained in step S8, preferably on table Tdec in the case indicated above in relation with step S6 where the orientation of the projection straight line is chosen according to the axis this straight line is most parallel to. This index ANSirisk is typically determined in the following manner: first, one determines the number $a_1$ of values in the table Tdec which are greater than a predetermined number rstart, the number $a_2$ of values in the table Tdec which are greater than rstart+1, the number $a_3$ of values in the table Tdec which are greater than rstart+2, . . . , and the number $a_{rstop-rstart}$ of values in the table Tdec which are greater than rstop, where rstop is also a predetermined number. Then, a weighted average of the numbers $a_i$ is calculated:

$$ANSirisk = \frac{\sum_{i=1}^{rstop-rstart} a_i \cdot (rstart + i)}{\sum_{i=1}^{rstop-rstart} (rstart + i)}$$

Preferred relations for determining the numbers rstart and rstop are given below:

$rstart=|\text{Floor}(3.1\sqrt{|Rcenter-R|}+2.1$
$\sqrt{|Vcenter-N|}+RstCenter-26)|$ $rstop=\text{Floor}(-rstart+0.5|RstCenter-3.95-1.43rstart|+$
$RstCenter+16)$ where, preferably, RstCenter=21, Rcenter=10 and Vcenter=30.

In step S13, the curves $ANSigram_1$ and $ANSigram_2$ and the indices $ANSindex_1$, $ANSindex_2$ and ANSirisk are displayed. Preferably, the first time-varying signal is also displayed.

Then the algorithm returns to step S2 for the next event in the time-varying signal acquired from the patient.

An example of a result obtained with the method according to the present embodiment will now be explained in relation with FIGS. 5 to 8.

In FIG. 5 is illustrated a signal representing the RR intervals of a healthy patient during a period of five minutes. Between instants $t_0$ and $t_1$ in this period, a tilt test is applied to the patient. As can be seen, a change of pace occurs in the RR intervals between the instants $t_0$ and $t_1$. However, in practice, such a change of pace can be detected on the RR interval signal only a certain time after the instant $t_0$, once the general decrease of the signal is distinguishable. In the example of FIG. 5, the instant from which one can observe, with the sole use of conventional means, that a change of pace has occurred is about an instant designated by $t_2$ which is relatively close to the instant $t_1$. It is also to be mentioned that, for certain patients, a tilt test does not always cause a clear change of pace in the RR intervals, hence the difficulty of detecting the change.

Figure 6:
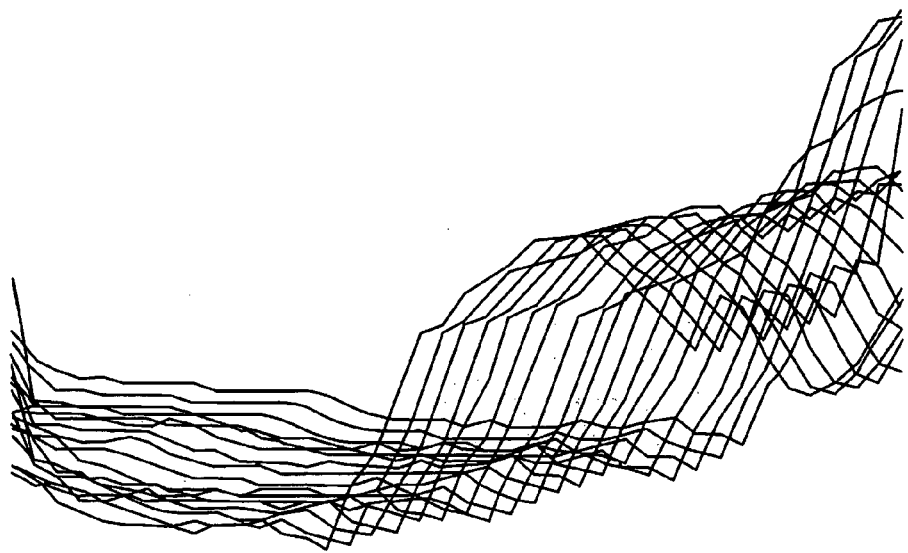
FIG. 6 shows a superposition of curves obtained by the method according to an embodiment of the invention and each representing an instantaneous state of what is believed to be the parasympathetic component of the ANS.

FIG. 6 shows a superposition of the curves $ANSigram_1$ obtained during the tilt test between the instants $t_0$ and $t_1$. Each one of these curves is a "photography" of the instantaneous state of what is believed to be the parasympathetic component of the ANS after a beating of the patient's heart or, more precisely, after an RR interval has been determined. In FIG. 6, the darker a curve is, the more recent it is. It can be seen that the shape of the curve $ANSigram_1$ evolves rapidly between the instants $t_0$ and $t_1$, which means that the method according to the invention is very reactive. As only the morphology of this curve is significant, no scale is needed, an aspect ratio being however predetermined for displaying the curve.

Figure 7:
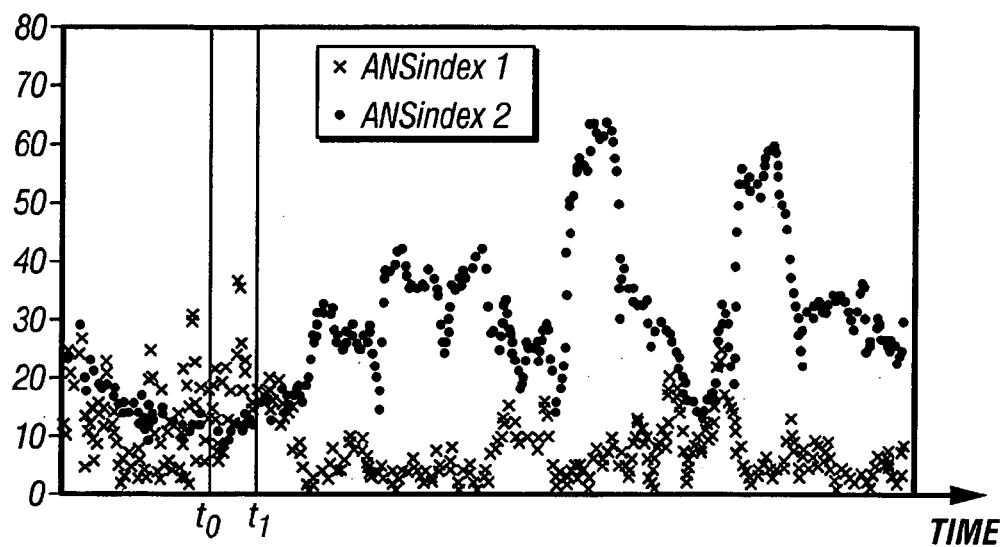
FIG. 7 shows the time variations of two indices obtained by the method according to an embodiment of the invention.

FIG. 7 shows on a same diagram a series of indices $ANSindex_1$ and a series of indices $ANSindex_2$ obtained during the above-mentioned five-minute period. The indices $ANSindex_1$ are represented by crosses and the indices $ANSindex_2$ by rectangles. It is interesting to note that the index $ANSindex_1$ increases at the beginning of the tilt and reaches a peak well before the instant $t_1$ at which the patient is at the 80° position and even well before the aforementioned instant $t_2$ observed with the traditional means, whereas the index $ANSindex_2$ increases slowly at the beginning of the tilt, until a first peak situated well after the instant $t_1$. Thus, the index $ANSindex_1$ reacts rapidly whereas the index $ANSindex_2$ has a slower reaction. Once the patient has reached the position at 80°, the index $ANSindex_1$ decreases while the index $ANSindex_2$ takes over and exhibits different waves. All this is perfectly coherent with what is currently known on the behaviors of the sympathetic and parasympathetic subsystems. In particular, the presence of the aforementioned waves in the index $ANSindex_2$ can be explained by the release of catecholamine hormones by the sympathetic subsystem.

Figure 8:
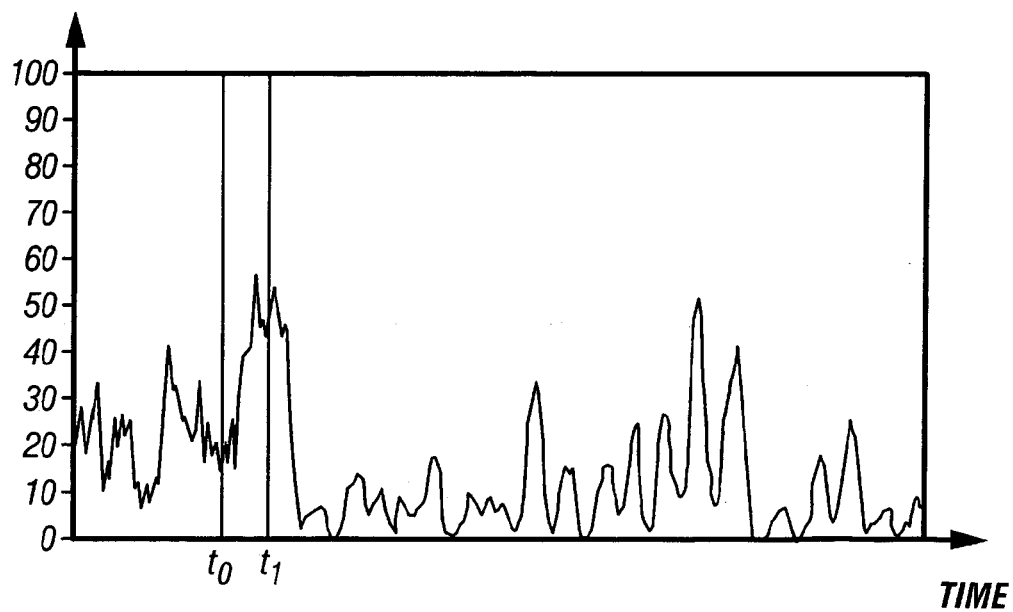
FIG. 8 shows the time variation of another index obtained by the method according to an embodiment of the invention.

FIG. 8 shows the evolution of the index ANSirisk during the above-mentioned five-minute period. One can see that this index exhibits a peak substantially in the middle of the tilt period between instants $t_0$ and $t_1$. In practice, rather than being displayed as a curve as shown in FIG. 8, the index ANSirisk may be presented to the user in the form of a gauge moving upward and downward as a function of time.

Figure 9:
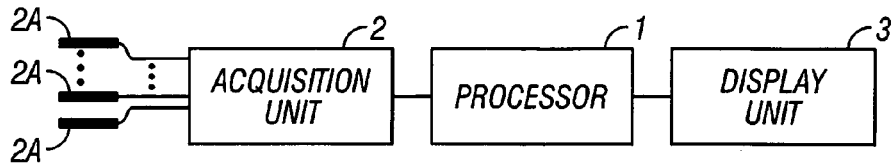
FIG. 9 is a block-diagram of a system in which the method according to an embodiment of the invention is implemented.

The method as described above is typically performed by a suitably programmed processor. As shown in FIG. 9, the processor, designated by reference 1, is connected via a suitable interface (not shown) to the output of an acquisition unit 2. The acquisition unit 2 is associated with electrodes 2a connected to the patient and performs analog-to-digital conversion to produce the first time-varying signal representing the quasi-periodical events. The acquisition unit 2 is, for example, an ECG unit. A display unit 3 is connected to the processor 1 to display the results provided by the method according to the invention, such as the curves $ANSigram_1$ and $ANSigram_2$, the difference between these curves $ANSigram_1$ and $ANSigram_2$, the indices $ANSindex_1$ and $ANSindex_2$, a historical record of these indices $ANSindex_1$ and $ANSindex_2$ (see FIG. 7), and/or the index ANSirisk, as well as the first time-varying signal.

In practice, several embodiments are possible for arranging the units 1, 2, 3 relative to one another. According to a first embodiment, the processor 1 and the display unit 3 are part of a laptop computer connected, for example via a USB port, to the acquisition unit 2. According to a second embodiment, the processor 1 is part of a plug-in electronic board. According to a third embodiment, the processor 1, the acquisition unit 2 and the display unit 3 are part of a stand-alone apparatus further comprising a main board, a printer, a media recorder (CD-ROM, . . . ), a battery, etc. According to a fourth embodiment, the processor 1 and the display unit 3 are part of a handheld device such as, for example, a cell phone, a Palm OS (registered trademark) device, a PocketPC (registered trademark) device, any personal digital assistant, etc.

Furthermore, in some embodiments, the connection between the electrodes 2a and the acquisition unit 2, that between the acquisition unit 2 and the processor 1, and/or that between the processor 1 and the display unit 3 may be wireless connections, such as Bluetooth (registered trademark) connections.

With reference to the flow diagram of FIG. 1, indices $ANSindex_1$ and $ANSindex_2$ are calculated in step S11 after combining the tables Cinc and Cdec with the upper envelopes ForwHull and BackwHull in step S10 and obtaining $ANSigram_1$ and $ANSigram_2$. This provides the information on the state of the first system. Other ways of extracting the state information of the first system may be used. Several additional examples are provided below.

Figure 10:
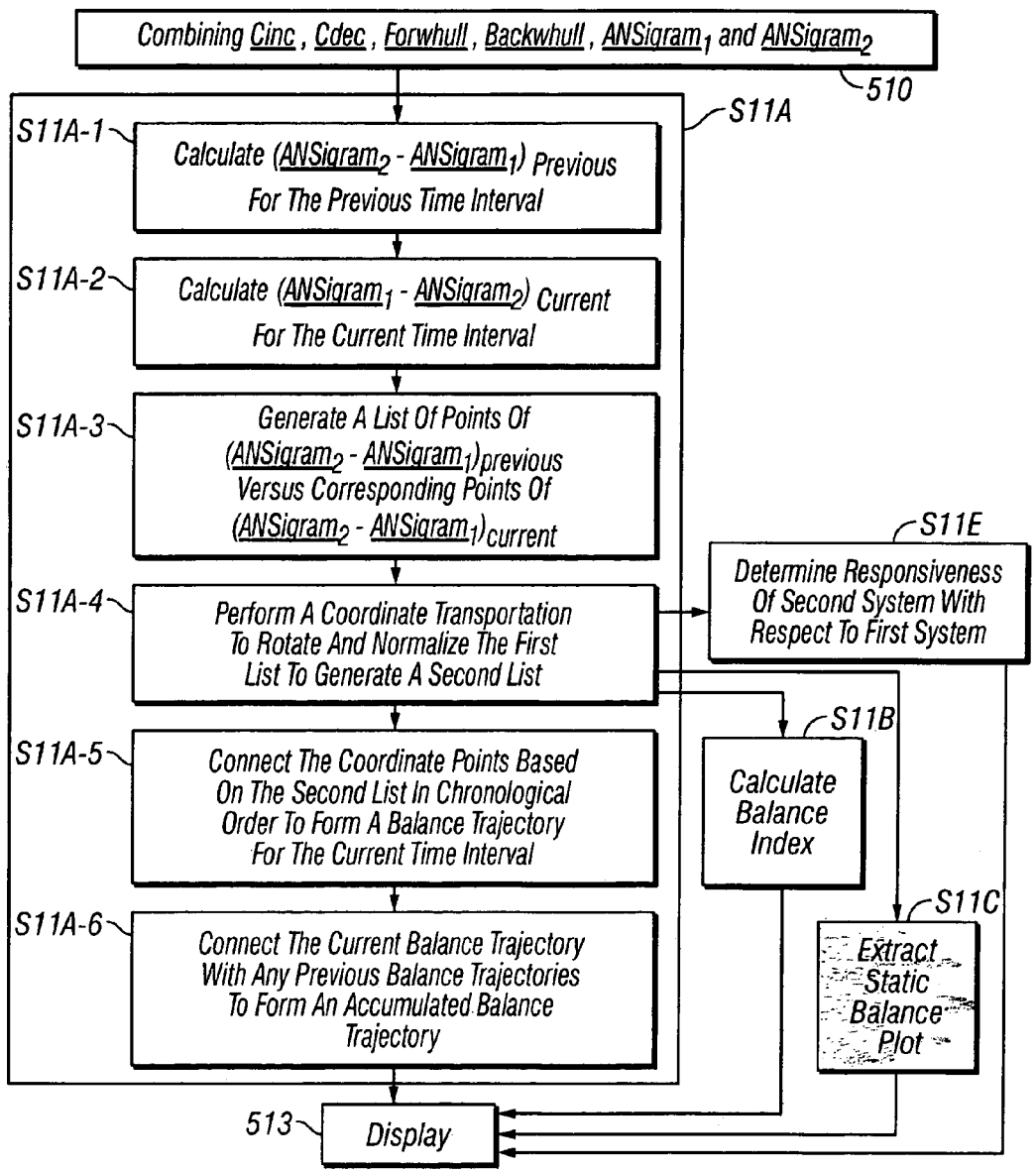
FIG. 10 is a flow diagram of a method of generating a balance trajectory according to another embodiment of the invention.
Figure 11:
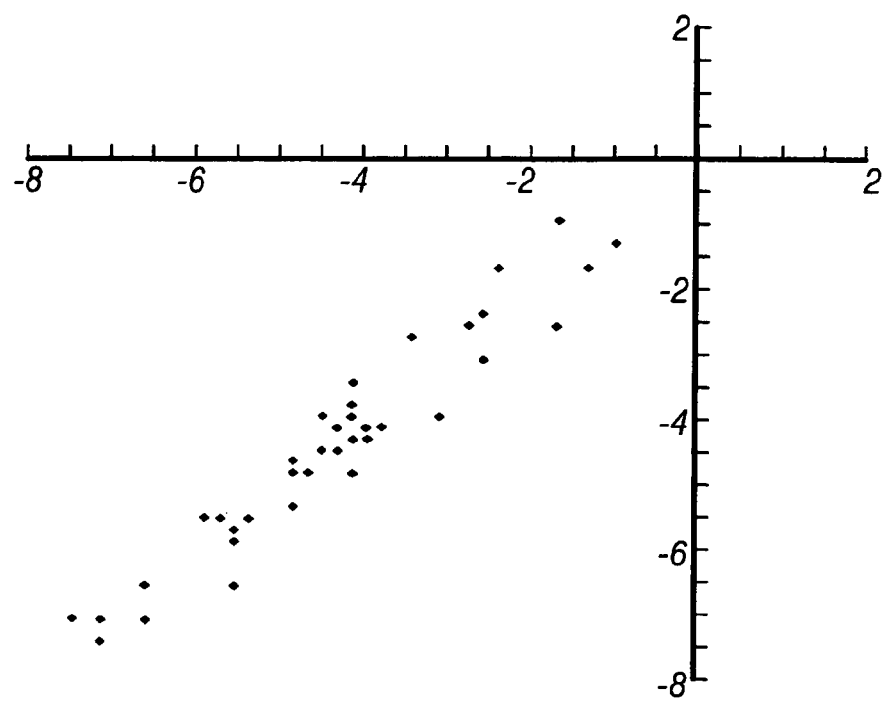
FIG. 11 is a plot of state tables according to one embodiment of the invention.
Figure 12:
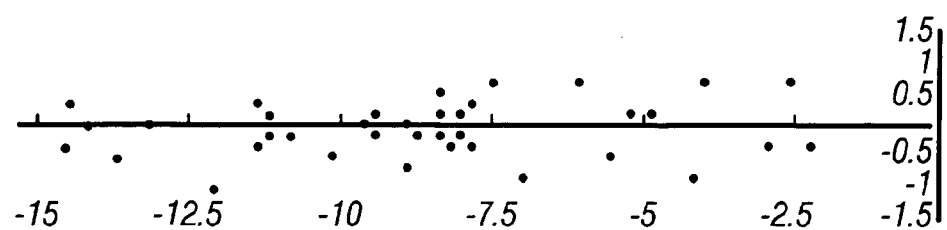
FIG. 12 is a rotated and normalized plot of the plot of FIG. 11 according to another embodiment of the invention.
Figure 13A:
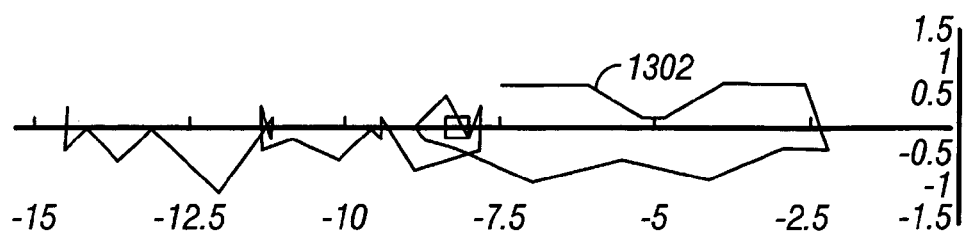
FIGS. 13a and 13b show two balance trajectories for two consecutive time intervals according to an embodiment of the invention.
Figure 13B:
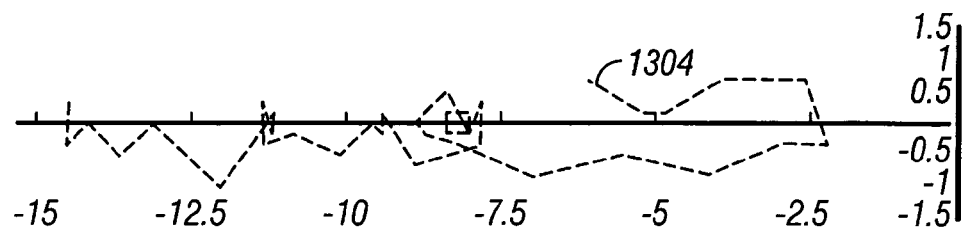

In one alternative extraction technique, a balance curve or trajectory is generated (step S11a). As seen in FIG. 10, $(ANSigram_2-ANSigram_1)_{previous}$ is computed by performing a point-by-point subtraction of the two tables (or vectors) using values ending with a previous time interval that immediately precedes the current time interval (step S11a-1). In step S11a-2, $(ANSigram_2-ANSigram_1)_{current}$ is computed by performing a point-by-point subtraction of the two tables using values ending with the current time interval. Steps S11a-1 and S11a-2 may be performed in any order or concurrently. In step S11a-3, a list of points of $(ANSigram_2-ANSigram_1)_{previous}$ and corresponding points of $(ANSigram_2-ANSigram_1)_{current}$ is generated. In addition, a plot of $(ANSigram_2-ANSigram_1)_{previous}$ in the x-axis versus $(ANSigram_2-ANSigram_1)_{current}$ in the y-axis may be made, as shown in FIG. 11, although it is not required to do so. In step S11a-4, the plot (or list) in S11a-3 is rotated and normalized via a coordinate transformation that takes the previous x-axis and y-axis and generate a new plot (or list) having (y+x) in the new x-axis and (y−x) in the new y-axis, as seen in FIG. 12. Hence, the new x-axis represents $(ANSigram_2-ANSigram_1)_{current}+(ANSigram_2-ANSigram_1)_{previous}$, while the new y-axis represent $(ANSigram_2-ANSigram_1)_{current}-(ANSigram_2-ANSigram_1)_{previous}$. This produces a rotation of −45° and scaling by a factor of $\sqrt{2}$. The range of values along the x-axis of the points in FIG. 12 are typically normalized to be between −50 and +50. In step S11a-5, the data points are connected in chronological order to produce a balance trajectory or curve for the current time interval. FIGS. 13a and 13b show an example of balance curves 1302, 1304 for two consecutive time intervals. The balance curves 1302, 1304 typically stay close to the x-axis, move primarily in the left and right directions, and may or may not cross the y-axis between the positive and negative regions of the x-axis. In the context of the ANS with the sympathetic part (SP) and the parasympathetic part (PSP), steps S11a-3 to S11a-5 start with a two-dimension representation and generate a representation with respect to a one-dimensional SP-PSP axis in a momentum space as shown in FIGS. 13a and 13b. The PSP is predominant to the left of the y-axis, while the SP is predominant to the right of the y-axis. The balance curves 1302, 1304 as shown are formed by connecting the discrete points by straight lines. In alternate embodiments, the balance curves 1302, 1304 may be formed by connecting the points by curve-fitting (e.g., spline).

Figure 14:
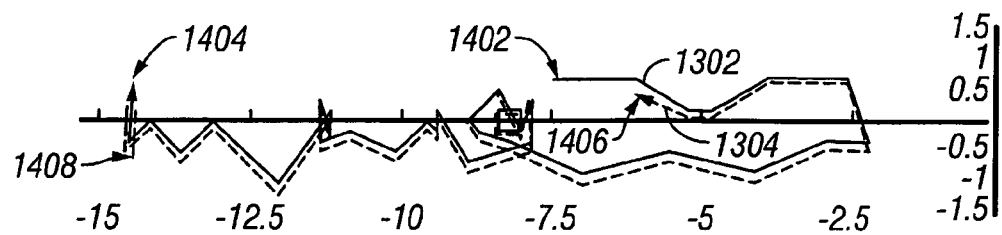
FIG. 14 shows connecting the two balance trajectories of FIGS. 13a and 13b.

In step S11a-6, an accumulated balance trajectory or curve is generated by combining the current balance curve with any preceding balance curve(s). FIG. 14 shows an example of connecting two balance curves resulting from data ending with two time intervals. The previous balance curve 1302 starts from a position 1402 where the value on the x-axis is about −7.5 and terminates at a position 1404 where the x-axis value is about −14.5. The current balance curve 1304 starts from a position 1406 where the x-axis value is about −6.1 and terminates at a position 1408 where the x-axis value is about −14.6. In connecting the balance curves, a time reversal is performed. The end point 1404 of the previous balance curve 1302 is connected to the end point 1408 of the current balance curve 1304, so that the start point 1406 of the current balance curve 1304 becomes the new end point of the connected, accumulated balance curve. For connecting additional balance curves, the time reversal is performed. As seen in FIG. 10, the accumulated balance curve can be displayed in step S13.

The tables $ANSigram_1$ and $ANSigram_2$, as discrete functions, help define the sympathovagal balance as a trajectory: the discrete points, with coordinates obtained from a representation of the point-by-point subtraction of the discrete functions of sympathetic (SP) and the parasympathetic (PSP), form as joined a rectifiable trajectory with illusion of non-fractal continuity. Only on the long term and with unique consideration of the discrete points is the fractal nature of space revealed through what the inventors term a static autonomic balance.

A subset balance trajectory or curve may be formed using the balance trajectories for different time intervals. In one example, one point can be selected from each balance trajectory based on a preset criterion, and the selected points of the plurality of balance trajectories can be connected together in chronological order to form the subset balance trajectory. For instance, the one point of a particular balance trajectory may be a point in the middle of the series of points that make up that balance trajectory. The subset balance trajectory provides another form of state information gleaned from the balance trajectories over a plurality of time intervals based on a criterion set by the user.

Another state information of the first system that can be extracted is the Balance Index, which is calculated as follows:

$$\text{Balance Index} = \text{Norm} * \text{sign of } (x_{CG} + y_{CG})$$

where $x_{CG}$ and $y_{CG}$ are x and y coordinates of a center of gravity point of all the points of the state tables $\text{ANSigram}_1$ and $\text{ANSigram}_2$ in the rotated and normalized coordinate system after step S11a-4 (e.g., FIG. 12) over a predetermined number of time intervals (e.g., eight time intervals), and wherein Norm is the distance from the original to the center of gravity point, as expressed below:

$$x_{CG} = \sum_{i=1}^{l} \frac{x_i}{l}$$

$$y_{CG} = \sum_{i=1}^{l} \frac{y_i}{l}$$

$$\text{Norm} = \sqrt{x_{CG}^2 + y_{CG}^2}$$

where "l" is the number of points in the table.

Figure 15:
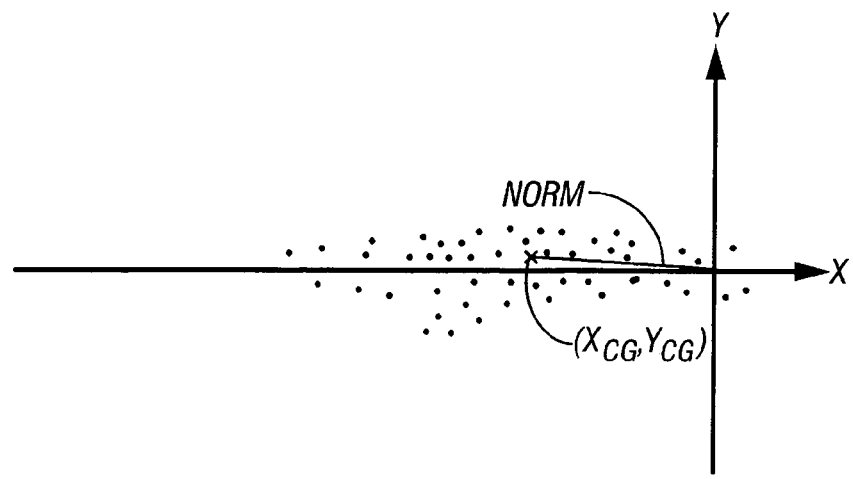
FIG. 15 is a plot illustrating mean average coordinates and a norm of the points for the rotated and normalized state tables over a plurality of time intervals according to an embodiment of the invention.

FIG. 15 shows an example of $x_{CG}$, $y_{CG}$, and Norm for the rotated and normalized state tables over eight time intervals. In the ANS context, a positive Balance Index indicates a sympathetic predominance over the time intervals selected while a negative Balance Index indicates a parasympathetic predominance, and the magnitude or absolute value of the Balance Index represents the strength of the predominance. The extraction of the Balance Index is shown in FIG. 10 as step S11b following the coordinate transformation of step S11a-4, and the result can be displayed in step S13.

Figure 16:
FIG. 16 is a plot showing static balance points in the rotated and normalized coordinate system.

The next state information that can be extracted is the static balance plot. FIG. 16 shows a plot displaying all the points of the state tables in the rotated and normalized coordinates, similar to the plot in FIG. 12 or FIG. 15, but for a much greater number of time intervals, such as hundreds of time intervals (e.g., 526 time intervals in FIG. 16). The static balance plot represents a static state or condition, unlike the dynamic changes that are represented by, for example, the balance trajectories and the Balance Index. The extraction of the static balance plot is shown in FIG. 10 as step S11c following the coordinate transformation of step S11a-4, and the result can be displayed in step S13.

In another embodiment, an alternative way is used to calculating the indices $\text{ANSindex}_1$ and $\text{ANSindex}_2$ in step S11 of FIG. 10. These alternate indices are defined as follows:

$$\text{ANSindex}_1 = c_1 + c_2 * a_1 + c_3 * b_1$$

$$\text{ANSindex}_2 = c_4 + c_5 * a_2 + c_6 * b_2$$

where $$a_1 = \underline{\text{ANSigram}}_1 \left[ l - \left[\frac{l}{n}\right]_t - 1 \right]$$

$$b_1 = \underline{\text{ANSigram}}_1 \left[ \left[\frac{l}{n}\right]_t + 1 \right]$$

$$a_2 = \underline{\text{ANSigram}}_2 \left[ l - \left[\frac{l}{n}\right]_t - 1 \right]$$

$$b_2 = \underline{\text{ANSigram}}_2 \left[ \left[\frac{l}{n}\right]_t + 1 \right]$$

wherein "l" is the number of terms in the corresponding table ANSigram, "n" is a number that is determined empirically and is 13 in the ANS context described herein. The term $[l/n]_t$ is the integer component of the ratio of l/n. The term $[l-[l/n]_t-1]$ is a rank representing the rank or position of the element of the table ANSigram to be selected. The term $[[l/n]_t+1]$ is another rank of the table ANSigram. The constants $c_1$ to $c_6$ can be determined or specified by the user for different applications, conditions, or the like. In one specific embodiment, the constants are: $c_1 = -190.857$, $c_2 = 3.54654$, $c_3 = -0.6894$, $c_4 = -87.7243$, $c_5 = 1.8054$, and $c_6 = -0.350946$.

These new indices can be used to characterize, for example, autonomic dysfunction by evaluating how associated or coupled the indices $\text{ANSindex}_1$ and $\text{ANSindex}_2$ are with respect to each other. The strong coupling or association indicates the absence of autonomic dysfunction, while a week coupling indicates the presence of autonomic dysfunction. The degree of coupling may be determined by (but not limited to) considering the average distance between the two indices over a number of time intervals. If the average distance is smaller than a preset threshold, the coupling is strong; if the average distance is greater than that preset threshold of another higher threshold, the coupling is weak. In one preferred embodiment, eight time intervals are used, and the preset threshold is about 1.7. In that case, the coupling is considered strong for approximately five time intervals in the middle of the eight time interval span if the average distance is smaller than about 1.7.

Figure 17:
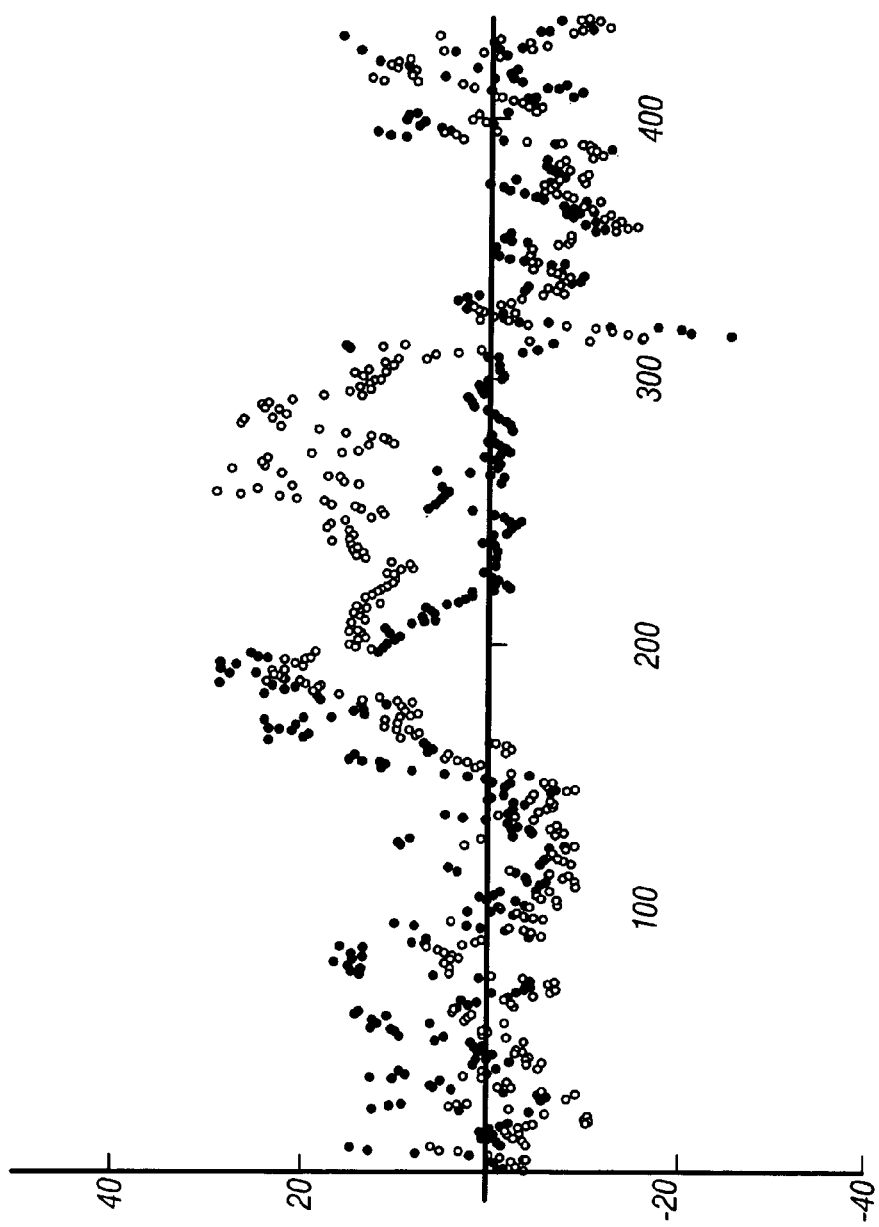
FIG. 17 is a plot showing the time variations of two indices obtain by a method according to another embodiment of the present invention.

FIG. 17 shows the time variations of the two indices $\text{ANSindex}_1$ and $\text{ANSindex}_2$ calculated according to this alternative method. The plot of FIG. 17 represents the evolution throughout time (during around 4 minutes and a half) of both the two indices for a case of isoproterenol injection (injection taking place just before time corresponding to the 200th RR interval). The black and gray dots correspond respectively to the degrees of activity of the parasympathetic and sympathetic systems. A clear activation of the latter system is observed, as the medical understanding of this drug would suggest. Furthermore, one can distinguish behind this compared evolution, the association and dissociation behaviors in the interaction (or coupling) of the two systems.

Figure 18:
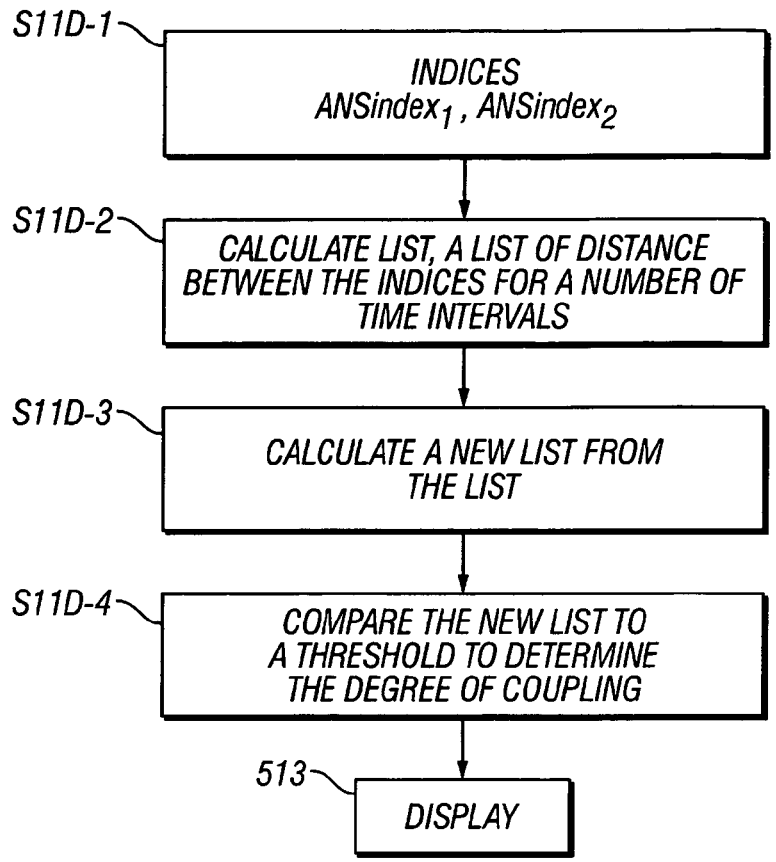
FIG. 18 is a flow diagram of a method of determining coupling between indices according to an embodiment of the invention.

FIG. 18 shows one method of determining the coupling between the indices. In step S11d-1 (which follows step S10 of FIG. 1), the new indices $ANSindex_1$ and $ANSindex_2$ are calculated. In step S11d-2, a List of distances between the indices is computed for a number of time intervals:

$$List = |ANSindex_1 - ANSindex_2|.$$

In step S11d-3, a New List is generated based on summing the List over a preset time window of w time intervals to provide a more global measure of the coupling by smoothing out local variations:

$$New\ List_j = \sum_{i=j}^{j+w} List_i$$

j=1 to (length of List-w).

In step S11d-4, the ratio (New List/w) is compared to a Threshold. If the ratio is greater than the Threshold, the coupling is weak; if the ratio is smaller than the Threshold, the coupling is strong, for a number of time intervals in the middle of the window over w time intervals. Threshold is set by the user and may be determined empirically. In one preferred embodiment as mentioned above, w=8 and Threshold=1.7.

Another state information that can be extracted is the responsiveness of the second system with respect to the first system, which may be determined based on a point-to-point comparison between a previous balance trajectory and a current balance trajectory. This is step S11-e in FIG. 10. To match the chronology of the points on the two trajectories, the end point (most recent) of the current balance trajectory and the start point (most ancient) of the previous balance trajectory are eliminated. The two trajectories are matched chronologically point-to-point, and the distances are calculated on the point-to-point basis. This determination provides a measure of the response of the second system with respect to what occurs in the first system. For example, the second system may represent the state of the heart or cardiac condition. The state information obtained is the responsiveness of the state of the heart with respect to activities in the ANS. This responsiveness characteristic involves a second order measurement based on evaluating first order measurements, namely, the balance trajectories, while a number of the state information parameters are obtained from first order measurement such as balance trajectory, balance index, and indices (e.g., $ANSindex_1$ and $ANSindex_2$).

Figure 19:
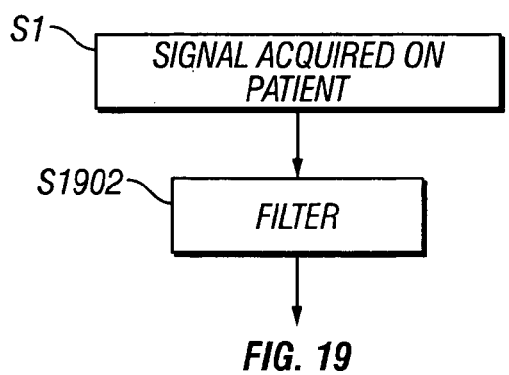
FIG. 19 is a flow diagram showing a filter for filtering input signal according to an embodiment of the invention.

Referring again to FIG. 10, an optional filter may be used to filter the signal acquired in step S1. As shown in FIG. 19, this step S1902 of filtering the signal can be used to filter out events that relate solely to the second system, such as a dysfunction in the second system. That is, the anomalous signal is not related to the periodic or quasi-periodic events produced by the second system from the first system. For example, the anomalous signal may represent an ectopic beat which is not an R wave. Any suitable filtering techniques can be used. For instance, one technique is based on some knowledge of what a normal R wave should appear geometrically (e.g., on the ECG), and filtering out the anomalous signal(s). Another filtering technique involves selecting the upper layer of the time series signal to identify the RR intervals while omitting the other layer(s) from anomalous signal(s). In this way, incorrect RR intervals due to the presence of the anomalous signals can be avoided as a result of filtering in step S1902.

The present embodiment as described above may be used in various applications, in particular in all situations where an evaluation of the ANS is expected for diagnostic or prognostic procedures concerning, for example:

1) Cardiology:
risk stratification (for arrhythmia, coronary diseases, arterial hypertension, etc.)
dosing beta-blockers
indication of pace maker of syncopic patient
prognostic factor of myocardial infarction 2) Endocrinology:
diabetology and risk assessment
evaluation of dysautonomia 3) Anesthesiology:
better dosing of analgesics and hypnotics
monitoring of cardio protection
evaluation of syncope risk during rachi-anesthesia and epidural anesthesia 4) Gynecology and Obstetrics:
fetal monitoring, detection of fetal distress 5) Pain Control and Therapy:
adapting dosage of analgesics
coupling with PCA (Patient Controlled Analgesia)
evaluation of pain in babies and children 6) Sleep Disease:
detection of SAS (sleep apnea)

7) Heart Transplant:
detection of rejection
evaluation of ANS reinnervation of the heart Although the invention has been described above in the context of the ANS, it will be clearly apparent to the skilled person that the principle of the invention may be applied to different systems than the ANS, in particular different biological systems, provided that the events in the original time-varying signal are quasi-periodical and that the corresponding series of time intervals is chaotic, i.e., strongly dependent on initial conditions.

It is to be understood that the above description is intended to be illustrative and not restrictive. Many embodiments will be apparent to those of skill in the art upon reviewing the above description. The scope of the invention should, therefore, be determined not with reference to the above description, but instead should be determined with reference to the appended claims along with their full scope of equivalents.

What is claimed is:

1. A method for analyzing the state of a first system from a time-varying signal representing a chaotic series of time intervals between quasi-periodical events produced by a second system governed by the first system, the method comprising:
extracting envelope information from the time-varying signal;
constructing a phase space for the time-varying signal;
extracting information on the relative positions of points corresponding to the time-varying signal in the phase space;
combining the envelope and the position information;
based on the combining, providing information relating to the state of the first system; and
displaying, via a display unit, information relating to the state of the first system.

2. The method according to claim 1, wherein the extracting envelope information, constructing, extracting information on the relative positions of points, combining, and providing information are repeated each time a new time interval appears in the time-varying signal.

3. The method according to claim 1, wherein extracting the envelope information comprises calculating a first upper envelope of the time-varying signal in the direction of the chronological order and calculating a second upper envelope of the time-varying signal in the direction opposite to the chronological order.

4. The method according to claim 1, wherein constructing the phase space comprises constructing vectors on the basis of values taken by the time-varying signal using a determined dimension for the phase space and a determined time lag.

5. The method according to claim 1, wherein extracting information on the relative positions of points comprises projecting said points corresponding to the time-varying signal in the phase space onto a lower-dimension space on which an order relation can be established, and calculating distances between the projected points.

6. The method according to claim 5, wherein extracting information on the relative positions of points further comprises discriminating positive and negative distances in said calculated distances.

7. The method according to claim 6, wherein an index representing a probability that a change of the state of the first system occurs at the next event is calculated based on said positive distances or said negative distances.

8. The method according to claim 1, wherein extracting information on the relative positions of points comprises projecting said points corresponding to the time-varying signal in the phase space onto a straight line that minimizes the average distance between said points and the straight line, and calculating distances between the projected points.

9. The method according to claim 8, wherein extracting information on the relative positions of points further comprises discriminating positive and negative distances in said calculated distances.

10. The method according to claim 9, wherein an index representing a probability that a change of the state of the first system occurs at the next event is calculated based on said positive distances or said negative distances.

11. The method according to claim 1, wherein the time-varying signal is a raw signal.

12. The method according to claim 1, wherein the first system is the autonomic nervous system.

13. The method according to claim 12, wherein the second system is the cardiac system, the quasi-periodical events are R waves of an electrocardiogram and the chaotic series of time intervals are RR intervals derived from said electrocardiogram.

14. The method according to claim 12, wherein combining comprises performing a first combination calculation providing first data representative of the parasympathetic component of the autonomic nervous system and performing a second combination calculation providing second data representative of the sympathetic component of the autonomic nervous system.

15. The method according to claim 14, wherein combining further comprises (1) calculating a first index representative of a complexity exponent of a first curve defined by said first data, or (2) calculating a second index representative of a complexity exponent of a second curve defined by said second data, or both (1) and (2).

16. The method according to claim 15, wherein combining further comprises (1) calculating a first index representative of a complexity exponent of a first curve defined by said first data, or (2) calculating a second index representative of a complexity exponent of a second curve defined by said second data, or both (1) and (2).

17. The method according to claim 12, wherein combining comprises performing a first combination calculation providing first data and performing a second combination calculation providing second data, the point-by-point subtraction of either of these first and second data from the other representing a sympathovagal balance between the parasympathetic and the sympathetic component of the first system which is the autonomic nervous system.

18. The method according to claim 1, wherein the first system is the autonomic nervous system; extracting envelope information comprises calculating a first upper envelope ForwHull of the time-varying signal in the direction of the chronological order and calculating a second upper envelope BackwHull of the time-varying signal in the direction opposite to the chronological order; extracting information on the relative positions of points comprises projecting said points corresponding to the time-varying signal in the phase space onto a lower-dimension space on which an order relation can be established, calculating distances between the projected points and discriminating positive and negative distances in said calculated distances, and combining comprises performing the following two combination calculations:

$$\underline{Coeffinc}_1 = B + (4 - 4A - 5B + 4AB) \cdot \underline{Cinc} - B \cdot \underline{Cdec}$$

$$\underline{Coeffdec}_1 = B - B \cdot \underline{Cinc} + (4A - 4AB - B) \cdot \underline{Cdec}$$

$$\underline{ANSigram}_1 = 1 - \frac{2 \cdot normcoeff}{3} \cdot (\underline{Coeffinc}_1 \cdot \underline{ForwHull} + \underline{Coeffdec}_1 \cdot \underline{BackwHull})$$

and $$\underline{Coeffinc}_2 = \frac{B}{3} + 4(1 - B) \cdot (1 - A) \cdot \underline{Cinc}$$

$$\underline{Coeffdec}_2 = \frac{B}{3} + 4(1 - B) \cdot A \cdot \underline{Cdec}$$

$$\underline{ANSigram}_2 = 1 - \frac{2 \cdot normcoeff}{3} \cdot (\underline{Coeffinc}_2 \cdot \underline{ForwHull} + \underline{Coeffdec}_2 \cdot \underline{BackwHull})$$

where A and B are predetermined constants, normcoeff is a normalization coefficient, and Cinc and Cdec are vectors representing respectively said positive and negative distances, and wherein said information provided in the step e) comprises the vectors $ANSigram_1$ and $ANSigram_2$.

19. The method according to claim 18, wherein combining further comprises calculating the following two indices:

$$ANSindex_1 = \text{Floor}\left[\left(6 + \frac{9375}{12} \cdot \left(\frac{\log(ANSlength_1)}{\log\sqrt{range_1^2 + N^2}} - 1\right)\right) \cdot (\sqrt{5} + 1)\right]$$

-continued $$ANSindex_2 = \text{Floor}\left[\left[\left(6+\frac{1875}{12}\cdot\left(\frac{\log(ANSlength_2)}{\log\sqrt{range_2^2+N^2}}-1.045\right)\right)\right]\cdot(\sqrt{5}+1)\right]$$

where Floor designates the integer part, which returns zero if the argument is negative, $ANSlength_1$ and $ANSlength_2$ respectively designate the length of a first curve defined by the vector $ANSigram_1$ and the length of a second curve defined by the vector $ANSigram_2$, $range_1$ designates the difference between the last value and the first value of the first curve, $range_2$ designates the difference between the last value and the first value of the second curve, and N designates a predetermined number equal to the dimension of the vectors $ANSigram_1$ and $ANSigram_2$.

20. The method according to claim 18, wherein combining further comprises:
   calculating $(ANSigram_2-ANSigram_1)_{previous}$ by performing a point-by-point subtraction of points in the vectors using values ending with a previous time interval that immediately precedes the current time interval;
   calculating $(ANSigram_2-ANSigram_1)_{current}$ by performing a point-by-point subtraction using values ending with the current time interval;
   generating a plot of $(ANSigram_2-ANSigram_1)_{previous}$ in an x-axis and $(ANSigram_2-ANSigram_1)_{current}$ in a y-axis; and
   performing a coordinate transformation of the plot to generate a rotated and normalized plot having $(ANSigram_2-ANSigram_1)_{current}+(ANSigram_2-ANSigram_1)_{previous}$ in a new x-axis and $(ANSigram_2-ANSigram_1)_{current}-(ANSigram_2-ANSigram_1)_{previous}$ in a new y-axis.

21. The method according to claim 20, wherein combining further comprising:
   generating the rotated and normalized plot for a plurality of consecutive time intervals;
   for each time interval, selecting a point from the plurality of points based on a preset criterion; and
   connecting the selected point between the time intervals in chronological order to form a subset balance curve.

22. The method according to claim 20, wherein combining further comprises generating a balance trajectory for a current time interval which includes:
   connecting points of the rotated and normalized plot in chronological order to produce a balance curve for the current time interval.

23. The method according to claim 22, wherein combining further comprises:
   generating a plurality of balance trajectories for a plurality of consecutive time intervals; and connecting the plurality of balance trajectories from end point to end point in chronological order of the consecutive time intervals with a time reversal in alternative order to form an accumulated balance trajectory.

24. The method according to claim 22, wherein combining further comprises:
   generating a pair of balance trajectories for two consecutive time intervals; and
   performing a point-to-point comparison between the two balance trajectories for points with matching time chronology from the two balance trajectories to determine a measure of response of the second system with respect to the first system,
   wherein the point-to-point comparison includes computing a distance between corresponding points from the two balance trajectories.

25. The method according to claim 22, further comprising displaying the balance curve.

26. The method according to claim 18, wherein combining further comprises:
   generating a rotated and normalized accumulated plot by calculating $(ANSigram_2-ANSigram_1)_{previous}$, calculating $ANSigram_2-ANSigram_1)_{current}$, generating a plot of $(ANSigram_2-ANSigram_1)_{previous}$ in an x-axis and $(ANSigram_2-ANSigram_1)_{current}$ in a y-axis, and performing a coordinate transformation of the plot to generate a rotated and normalized plot, for a plurality of time intervals; and
   calculating a Balance Index=Norm * sign of $(X_{CG}+Y_{CG})$ where $$x_{CG}=\sum_{i=1}^{l}\frac{x_i}{l}$$

$$y_{CG}=\sum_{i=1}^{l}\frac{y_i}{l}$$

$$\text{Norm}=\sqrt{x^2_{CG}+y^2_{CG}}$$

where "1" is the number of points in the vector $ANSigram_2$ or $ANSigram_1$.

27. The method according to claim 26, further comprising displaying the Balance Index.

28. The method according to claim 18, wherein combining further comprises:
   generating a rotated and normalized static balance plot by calculating $(ANSigram_2-ANSigram_1)_{previous}$, calculating $(ANSigram_2-ANSigram_1)_{current}$, generating a plot of $(ANSigram_2-ANSigram_1)_{previous}$ in an x-axis and $(ANSigram_2-ANSigram_1)_{current}$ in a y-axis, and performing a coordinate transformation of the plot to generate a rotated and normalized plot for a number of time intervals, the number being at least about 100.

29. The method according to claim 28, further comprising displaying the rotated and normalized static balance plot.

30. The method according to claim 18, wherein combining further comprises calculating the following two indices:

$$ANSindex_1=c_1+c_2*a_1+c_3*b_1$$

$$ANSindex_2=c_4+c_5*a_2+c_6*b_2$$

where $$a_1=\frac{ANSigram_1}{}\left[l-\left[\frac{l}{n}\right]_l-1\right]$$

$$b_1=\frac{ANSigram_1}{}\left[\left[\frac{l}{n}\right]_l+1\right]$$

$$a_2=\frac{ANSigram_2}{}\left[l-\left[\frac{l}{n}\right]_l-1\right]$$

$$b_2=\frac{ANSigram_2}{}\left[\left[\frac{l}{n}\right]_l+1\right]$$

wherein "1" is the number of terms in a corresponding vector ANSigram, "n" is a preset integer number, $[1/n]_I$ is the integer component of the ratio of 1/n, $[1-[1/n]_I-1]$ is a rank representing the rank of an element of the corresponding vector ANSigram to be selected, and $[[1/n]_I+1]$ is another rank of the corresponding vector ANSigram.

31. The method according to claim 30, wherein n=13.

32. The method according to claim 30, wherein $c_1$=−190.857, $c_2$=3.54654, $c_3$=−0.6894, $c_4$=−87.7243, $c_5$=1.8054, and $c_6$=−0.350946.

33. The method according to claim 30, wherein combining further comprises determining a coupling between the two indices, $ANSindex_1$ and $ANSindex_2$.

34. The method according to claim 33, wherein determining the coupling comprises:
creating a List of distances between the two indices for a number of time intervals, List=|$ANSindex_1$−$ANSindex_2$|;
generating a New List based on summing the List over a preset time window of w time intervals to provide a more global measure of coupling, $$New\ List_j = \sum_{i=j}^{j+w} List_i$$

j=1 to (length of List−w); and
evaluating a coupling between the two indices by comparing (New List/w) with a threshold, where the coupling is strong if (New List/w) is smaller than the threshold and the coupling is weak if (New List/w) is greater than the threshold.

35. The method according to claim 33, further comprising displaying the coupling between the two indices, $ANSindex_1$ and $ANSindex_2$.

36. The method according to claim 1, further comprising filtering out an anomalous signal from the time-varying signal prior to extracting envelope information from the time-varying signal and constructing the phase space for the time-varying signal.

37. An apparatus for analyzing the state of a first system from a time-varying signal representing a chaotic series of time intervals between quasi-periodical events produced by a second system governed by the first system, the apparatus comprising:
a processor configured to: extract envelope information from the time-varying signal; construct a phase space for the time-varying signal; extract information on the relative positions of points corresponding to the time-varying signal in the phase space; combine the envelope and the position information; and, based on combining the envelope and the position information, provide information relating to the state of the first system; and
a display to display information relating to the state of the first system.

38. The apparatus according to claim 37, wherein the processor is configured to repeat extracting envelope information, constructing, extracting information on the relative positions of points, combining, and providing information, each time a new time interval appears in the time-varying signal.

39. The apparatus according to claim 37, wherein extracting the envelope information comprises calculating a first upper envelope of the time-varying signal in the direction of the chronological order and calculating a second upper envelope of the time-varying signal in the direction opposite to the chronological order.

40. The apparatus according to claim 37, wherein constructing the phase space comprises constructing vectors on the basis of values taken by the time-varying signal using a determined dimension for the phase space and a determined time lag.

41. The apparatus according to claim 37, wherein extracting information on the relative positions of points comprises projecting said points corresponding to the time-varying signal in the phase space onto a lower-dimension space on which an order relation can be established, and calculating distances between the projected points.

42. The apparatus according to claim 41, wherein extracting information on the relative positions of points further comprises discriminating positive and negative distances in said calculated distances.

43. The apparatus according to claim 42, wherein the processor is configured to calculate an index representing a probability that a change of the state of the first system occurs at the next event, based on said positive distances or said negative distances.

44. The apparatus according to claim 37, wherein extracting information on the relative positions of points comprises projecting said points corresponding to the time-varying signal in the phase space onto a straight line that minimizes the average distance between said points and the straight line, and calculating distances between the projected points.

45. The apparatus according to claim 44, wherein extracting information on the relative positions of points further comprises discriminating positive and negative distances in said calculated distances.

46. The apparatus according to claim 45, wherein the processor is configured to calculate an index representing a probability that a change of the state of the first system occurs at the next event, based on said positive distances or said negative distances.

47. The apparatus according to claim 37, wherein the first system is the autonomic nervous system.

48. The apparatus according to claim 47, wherein the second system is the cardiac system, the quasi-periodical events are R waves of an electrocardiogram and the chaotic series of time intervals are RR intervals derived from said electrocardiogram.

49. The apparatus according to claim 47, wherein combining the envelope and the position information comprises performing a first combination calculation providing first data representative of the parasympathetic component of the autonomic nervous system and performing a second combination calculation providing second data representative of the sympathetic component of the autonomic nervous system.

50. The apparatus according to claim 49, wherein combining the envelope and the position information further comprises (1) calculating a first index representative of a complexity exponent of a first curve defined by said first data, or (2) calculating a second index representative of a complexity exponent of a second curve defined by said second data, or both (1) and (2).

51. The apparatus according to claim 47, wherein combining the envelope and the position information comprises performing a first combination calculation providing first data and performing a second combination calculation providing second data, the point-by-point subtraction of either of these first and second data from the other representing a sympathovagal balance between the parasympathetic and the sympathetic component of the first system which is the autonomic nervous system.

52. The apparatus according to claim 51, wherein combining the envelope and the position information further comprises (1) calculating a first index representative of a complexity exponent of a first curve defined by said first data, or (2) calculating a second index representative of a complexity exponent of a second curve defined by said second data, or both (1) and (2).

53. The apparatus according to claim 37, wherein the first system is the autonomic nervous system; extracting envelope information comprises calculating a first upper envelope ForwHull of the time-varying signal in the direction of the chronological order and calculating a second upper envelope BackwHull of the time-varying signal in the direction opposite to the chronological order; extracting information on the relative positions of points comprises projecting said points corresponding to the time-varying signal in the phase space onto a lower-dimension space on which an order relation can be established, calculating distances between the projected points and discriminating positive and negative distances in said calculated distances, and combining comprises performing the following two combination calculations:

$$Coeffinc_1 = B + (4 - 4A - 5B + 4AB) \cdot Cinc - B \cdot Cdec$$

$$Coeffdec_1 = B - B \cdot Cinc + (4A - 4AB - B) \cdot Cdec$$

$$ANSigram_1 = 1 - \frac{2 \cdot normcoeff}{3} \cdot (Coeffinc_1 \cdot ForwHull + Coeffdec_1 \cdot BackwHull)$$

and $$Coeffinc_2 = \frac{B}{3} + 4(1-B) \cdot (1-A) \cdot Cinc$$

$$Coeffdec_2 = \frac{B}{3} + 4(1-B) \cdot A \cdot Cdec$$

$$ANSigram_2 = 1 - \frac{2 \cdot normcoeff}{3} \cdot (Coeffinc_2 \cdot ForwHull + Coeffdec_2 \cdot BackwHull)$$

where A and B are predetermined constants, normcoeff is a normalization coefficient, and Cinc and Cdec are vectors representing respectively said positive and negative distances, and wherein said information provided in the step e) comprises the vectors $ANSigram_1$ and $ANSigram_2$.

54. The apparatus according to claim 37, further comprising a filter to filter out an anomalous signal from the time-varying signal prior to extracting envelope information from the time-varying signal and constructing the phase space for the time-varying signal.

55. A computer readable storage medium having a computer program for analyzing the state of a first system from a time-varying signal representing a chaotic series of time intervals between quasi-periodical events produced by a second system governed by the first system, the computer program comprising:
    code for extracting envelope information from the time-varying signal;
    code for constructing a phase space for the time-varying signal;
    code for extracting information on the relative positions of points corresponding to the time-varying signal in the phase space;
    code for combining the envelope and the position information;
    code for, based on the combining, providing information relating to the state of the first system; and
    code for displaying information relating to the state of the first system.

56. The computer readable storage medium according to claim 55, wherein the computer program further comprises code for repeating extracting envelope information, constructing, extracting information on the relative positions of points, combining, and providing information, each time a new time interval appears in the time-varying signal.

57. The computer readable storage medium according to claim 55, wherein the computer program further comprises code for filtering out an anomalous signal from the time-varying signal prior to extracting envelope information from the time-varying signal and constructing the phase space for the time-varying signal.

58. A method for analyzing the state of a first system from a time-varying signal representing a chaotic series of time intervals between quasi-periodical events produced by a second system governed by the first system, the method comprising:
    obtaining the time-varying signal from a patient via an acquisition unit;
    extracting envelope information from the time-varying signal;
    constructing a phase space for the time-varying signal;
    extracting information on the relative positions of points corresponding to the time-varying signal in the phase space;
    combining the envelope and the position information; and
    based on the combining, providing information relating to the state of the first system;
    wherein the first system is the autonomic nervous system of the patient; and
    wherein the second system is the cardiac system of the patient, the quasi-periodical events are R waves of an electrocardiogram of the patient, and the chaotic series of time intervals are RR intervals derived from said electrocardiogram.

59. A method for analyzing the state of a first system from a time-varying signal representing a chaotic series of time intervals between quasi-periodical events produced by a second system governed by the first system, the method comprising:
    obtaining the time-varying signal from a patient via an acquisition unit;
    extracting envelope information from the time-varying signal;
    constructing a phase space for the time-varying signal;
    extracting information on the relative positions of points corresponding to the time-varying signal in the phase space;
    combining the envelope and the position information; and
    based on the combining, providing information relating to the state of the first system;
    wherein the first system is the autonomic nervous system of the patient; and
    wherein combining comprises performing a first combination calculation providing first data representative of the parasympathetic component of the autonomic nervous system of the patient and performing a second combination calculation providing second data representative of the sympathetic component of the autonomic nervous system of the patient.

60. The method according to claim 59, wherein the first system is the autonomic nervous system; extracting envelope information comprises calculating a first upper envelope ForwHull of the time-varying signal in the direction of the chronological order and calculating a second upper envelope BackwHull of the time-varying signal in the direction opposite to the chronological order; extracting information on the relative positions of points comprises projecting said points corresponding to the time-varying signal in the phase space onto a lower-dimension space on which an order relation can be established, calculating distances between the projected points and discriminating positive and negative distances in said calculated distances, and combining comprises performing the following two combination calculations:

$$Coeffinc_1 = B + (4 - 4A - 5B + 4AB) \cdot Cinc - B \cdot Cdec$$

$$Coeffdec_1 = B - B \cdot Cinc + (4A - 4AB - B) \cdot Cdec$$

$$ANSigram_1 = 1 - \frac{2 \cdot normcoeff}{3} \cdot (Coeffinc_1 \cdot ForwHull + Coeffdec_1 \cdot BackwHull)$$

and $$Coeffinc_2 = \frac{B}{3} + 4(1 - B) \cdot (1 - A) \cdot Cinc$$

$$Coeffdec_2 = \frac{B}{3} + 4(1 - B) \cdot A \cdot Cdec$$

$$ANSigram_2 = 1 - \frac{2 \cdot normcoeff}{3} \cdot (Coeffinc_2 \cdot ForwHull + Coeffdec_2 \cdot BackwHull)$$

where A and B are predetermined constants, normcoeff is a normalization coefficient, and Cinc and Cdec are vectors representing respectively said positive and negative distances, and wherein said information provided in the step e) comprises the vectors $ANSigram_1$ and $ANSigram_2$.

61. The method according to claim 60, wherein combining further comprises calculating the following two indices:

$$ANSindex_1 = c_1 + c_2 * a_1 + c_3 * b_1$$

$$ANSindex_2 = c_4 + c_5 * a_2 + c_6 * b_2$$

where $$a_1 = \overline{ANSigram_1 \left[ l - \left[ \frac{l}{n} \right]_I - 1 \right]}$$

$$b_1 = \overline{ANSigram_1 \left[ \left[ \frac{l}{n} \right]_I + 1 \right]}$$

$$a_2 = \overline{ANSigram_2 \left[ l - \left[ \frac{l}{n} \right]_I - 1 \right]}$$

$$b_2 = \overline{ANSigram_2 \left[ \left[ \frac{l}{n} \right]_I + 1 \right]}$$

wherein "1" is the number of terms in a corresponding vector ANSigram, "n" is a preset integer number, $[l/n]_I$ is the integer component of the ratio of $l/n$, $[1-[l/n]_I-1]$ is a rank representing the rank of an element of the corresponding vector ANSigram to be selected, and $[[l/n]_I+1]$ is another rank of the corresponding vector ANSigram.

62. A method for analyzing the state of a first system from a time-varying signal representing a chaotic series of time intervals between quasi-periodical events produced by a second system governed by the first system, the method comprising:

obtaining the time-varying signal from a patient via an acquisition unit;

extracting envelope information from the time-varying signal;

constructing a phase space for the time-varying signal;

extracting information on the relative positions of points corresponding to the time-varying signal in the phase space;

combining the envelope and the position information; and based on the combining, providing information relating to the state of the first system;

wherein the first system is the autonomic nervous system of the patient; and wherein combining comprises performing a first combination calculation providing first data and performing a second combination calculation providing second data, the point-by-point subtraction of either of these first and second data from the other representing a sympathovagal balance between the parasympathetic and the sympathetic component of the autonomic nervous system of the patient.

63. The method according to claim 62, wherein the first system is the autonomic nervous system; extracting envelope information comprises calculating a first upper envelope ForwHull of the time-varying signal in the direction of the chronological order and calculating a second upper envelope BackwHull of the time-varying signal in the direction opposite to the chronological order; extracting information on the relative positions of points comprises projecting said points corresponding to the time-varying signal in the phase space onto a lower-dimension space on which an order relation can be established, calculating distances between the projected points and discriminating positive and negative distances in said calculated distances, and combining comprises performing the following two combination calculations:

$$Coeffinc_1 = B + (4 - 4A - 5B + 4AB) \cdot Cinc - B \cdot Cdec$$

$$Coeffdec_1 = B - B \cdot Cinc + (4A - 4AB - B) \cdot Cdec$$

$$ANSigram_1 = 1 - \frac{2 \cdot normcoeff}{3} \cdot (Coeffinc_1 \cdot ForwHull + Coeffdec_1 \cdot BackwHull)$$

and $$Coeffinc_2 = \frac{B}{3} + 4(1 - B) \cdot (1 - A) \cdot Cinc$$

$$Coeffdec_2 = \frac{B}{3} + 4(1 - B) \cdot A \cdot Cdec$$

$$ANSigram_2 = 1 - \frac{2 \cdot normcoeff}{3} \cdot (Coeffinc_2 \cdot ForwHull + Coeffdec_2 \cdot BackwHull)$$

where A and B are predetermined constants, normcoeff is a normalization coefficient, and Cinc and Cdec are vectors representing respectively said positive and negative distances, and wherein said information provided in the step e) comprises the vectors $ANSigram_1$ and $ANSigram_2$.

64. The method according to claim 63, wherein combining further comprises calculating the following two indices:

$ANSindex_1 = c_1 + c_2 * a_1 + c_3 * b_1$ $ANSindex_2 = c_4 + c_5 * a_2 + c_6 * b_2$ where $$a_1 = \frac{ANSigram_1}{\left[\left[\frac{l}{n}\right]_I + 1\right]} \left[l - \left[\frac{l}{n}\right]_I - 1\right]$$

$$b_1 = \frac{ANSigram_1}{\left[\left[\frac{l}{n}\right]_I + 1\right]}$$

$$a_2 = \frac{ANSigram_2}{\left[\left[\frac{l}{n}\right]_I + 1\right]} \left[l - \left[\frac{l}{n}\right]_I - 1\right]$$

$$b_2 = \frac{ANSigram_2}{\left[\left[\frac{l}{n}\right]_I + 1\right]}$$

wherein "l" is the number of terms in a corresponding vector ANSigram, "n" is a preset integer number, $[l/n]_I$ is the integer component of the ratio of l/n, $[l-[l/n]_I-1]$ is a rank representing the rank of an element of the corresponding vector ANSigram to be selected, and $[[l/n]_I+1]$ is another rank of the corresponding vector ANSigram.

65. An apparatus for analyzing the state of a first system from a time-varying signal representing a chaotic series of time intervals between quasi-periodical events produced by a second system governed by the first system, the apparatus comprising:

means for extracting envelope information from the time-varying signal, constructing a phase space for the time-varying signal, extracting information on the relative positions of points corresponding to the time-varying signal in the phase space, combining the envelope and the position information, and, based on the combining, providing information relating to the state of the first system; and a display for displaying information relating to the state of the first system.

* * * * *